(12) United States Patent
Hsu et al.

(10) Patent No.: US 11,340,204 B2
(45) Date of Patent: May 24, 2022

(54) SYSTEM FOR MANAGING AND TRADING FRESH FOODS ACCORDING TO FLAVOR AND METHOD THEREOF

(71) Applicant: TAIWAN CARBON NANO TECHNOLOGY CORPORATION, Miaoli County (TW)

(72) Inventors: Ching-Tung Hsu, Miaoli County (TW); Chun-Wei Shih, Miaoli County (TW); Chao-Chieh Lin, Miaoli County (TW); Yuan-Shin Huang, Miaoli County (TW); Chia-Hung Li, Miaoli County (TW); Chun-Hsien Tsai, Miaoli County (TW); Chun-Jung Tsai, Miaoli County (TW)

(73) Assignee: TAIWAN CARBON NANO TECHNOLOGY CORPORATION, Miaoli County (TW)

( * ) Notice: Subject to any disclaimer, the term of this patent is extended or adjusted under 35 U.S.C. 154(b) by 12 days.

(21) Appl. No.: 17/142,506

(22) Filed: Jan. 6, 2021

(65) Prior Publication Data
US 2021/0223223 A1 Jul. 22, 2021

(30) Foreign Application Priority Data
Jan. 21, 2020 (TW) .................................. 109102196

(51) Int. Cl.
*G01N 21/78* (2006.01)
*G01N 33/02* (2006.01)
*G01N 21/25* (2006.01)
*G06Q 30/06* (2012.01)

(52) U.S. Cl.
CPC ......... *G01N 33/025* (2013.01); *G01N 21/251* (2013.01); *G06Q 30/0633* (2013.01)

(58) Field of Classification Search
CPC .. G06K 7/1417; G06K 7/10554; G01N 21/78; G01N 33/025; G01N 2021/7756; G06T 7/90; G06T 2207/10; G06T 2207/10024
See application file for complete search history.

(56) References Cited

U.S. PATENT DOCUMENTS

2020/0062456 A1\* 2/2020 Granevitze ............ B65D 85/80

\* cited by examiner

*Primary Examiner* — Abdullahi Nur
(74) *Attorney, Agent, or Firm* — Muncy, Geissler, Olds & Lowe, P.C.

(57) ABSTRACT

A system and a method for managing and trading fresh foods according to a flavor thereof, comprising a plurality of fresh foods, an image capturing module, a processing module and a classification module. The fresh food is attached with a product label including a code and a colorimetric transducer array that comprises at least one sensing material for sensing the fresh food. The sensing material undergoes a chemical reaction with at least one metabolic molecule of the fresh food to change the sensing material from an initial color to an indication color. The image capturing module captures an image comprising an appearance of the fresh food, the code and the indication color. The processing module provides a real-time information according to a comparison result between the image and a database. The classification module receives the real-time information and classifies the fresh food according to the real-time information.

9 Claims, 3 Drawing Sheets

SYSTEM FOR MANAGING AND TRADING FRESH FOODS ACCORDING TO FLAVOR AND METHOD THEREOF

FIELD OF THE INVENTION

The invention relates to a system and a method for managing and trading fresh foods, and more particularly to a system for managing and trading fresh foods according to a flavor and a method thereof.

BACKGROUND OF THE INVENTION

With the popularity of the Internet, social media and mobile phone among users, the way of using online platforms for transactions has gradually been accepted by products and services providers and consumers. Since online transactions are not restricted by region and time, a number of types of commodities that can be traded are much greater than the traditional channels, and trading via online transactions is more convenient and fast, it has occupied a considerable share of commercial transactions in recent years.

Related technologies for online transactions can be found in the U.S. Pat. No. 8,392,276 B1, which provides a technology that facilitates transactions of commodities between products and services providers and consumers, thereby increasing the share of online transactions. Related technologies can also be found in the U.S. Pat. No. 6,643,624 B2, which discloses a technology that allows consumers to use a single interface to conduct transactions with multiple interconnected networks.

However, for special commodity fields, such as fresh foods, an industry can only use words or pictures to convey a flavor of fresh foods, and words or pictures themselves have subjective consciousness, and even deviate from the actual flavor, and cannot objectively and fully convey the flavor of fresh foods. For this reason, it results in a cognitive gap between the industry and consumers. That is, a gap exists between the actual quality of fresh foods and the subjective expectations or demands of consumers, and consequently the demands of consumers are unable to be met. On the other hand, for the industry that trades fresh foods through online platforms, usually fresh foods can only be distinguished by time, variety, place of origin, weight or volume, etc. However, in fact, the quality of fresh foods is also related to other factors, in other words, even for the same batch of fresh foods with the same conditions as above, the quality will be different, thus it would be inappropriate if the same batch of fresh foods is still classified as a same product.

SUMMARY OF THE INVENTION

A main object of the invention is to solve the problem that the traditional fresh foods online traders are incapable of accurately providing consumers with flavor information of fresh foods, resulting in difficulty in gaining trust of consumers; and the problem that the traditional fresh foods online traders are incapable of accurately classifying when managing fresh foods.

In order to achieve the above object, the invention provides a system for managing foods according to a flavor thereof, comprising: a plurality of fresh foods, each of the plurality of fresh foods attached with a product label, the product label including a thin film, a code provided on the thin film and associated with each of the plurality of fresh foods, and a colorimetric transducer array formed on the thin film, the colorimetric transducer array comprising at least one sensing material for sensing the plurality of fresh foods, each of the at least one sensing material undergoing a chemical reaction with at least one metabolic molecule of each of the fresh foods to change each of the at least one sensing material from an initial color to an indication color; an image capturing module, capturing an image, the image comprising an appearance of each of the plurality of fresh foods, the code and the indication color; a processing module, providing a real-time information associated with a quality of each of the plurality of fresh foods according to a comparison result between the image and a database; and a classification module, receiving the real-time information and classifying the plurality of fresh foods according to the real-time information.

In order to achieve the above object, the invention further provides a method for managing foods according to a flavor thereof, comprising following steps of: providing a plurality of fresh foods, attaching a product label on each of the plurality of fresh foods, the product label comprising a thin film, a code provided on the thin film and associated with each of the plurality of fresh foods, and a colorimetric transducer array formed on the thin film, the colorimetric transducer array comprising at least one sensing material for sensing the plurality of fresh foods, each of the at least one sensing material undergoing a chemical reaction with at least one metabolic molecule of each of the plurality of fresh foods to change each of the at least one sensing material from an initial color to an indication color; capturing an image, the image comprising an appearance of each of the plurality of fresh foods, the code and the indication color; providing a real-time information associated with a quality of each of the plurality of fresh foods according to a comparison result between the image and a database; generating a classification result for the quality of each of the plurality of fresh foods according to the real-time information; and classifying each of the plurality of fresh foods according to the classification result.

In order to achieve the above object, the invention further provides a method for trading foods, comprising following steps of providing a plurality of fresh foods, attaching a product label on each of the plurality of fresh foods, the product label comprising a thin film, a code provided on the thin film and associated with each of the plurality of fresh foods, and a colorimetric transducer array formed on the thin film, the colorimetric transducer array comprising at least one sensing material for sensing each of the plurality of fresh foods, each of the at least one sensing material undergoing a chemical reaction with at least one metabolic molecule of each of the plurality of fresh foods to change each of the at least one sensing material from an initial color to an indication color; capturing an image, the image comprising an appearance of each of the plurality of fresh foods, the code and the indication color; providing a real-time information associated with a quality of each of the plurality of fresh foods according to a comparison result between the image and a database; generating a classification result for the quality of each of the plurality of fresh foods according to the real-time information; and using the classification result as a part of a sales information of each of the plurality of fresh foods and displaying the classification result to at least one consumer for selecting and purchasing each of the plurality of fresh foods according to the classification result.

Accordingly, by coordinating the colorimetric transducer array with the image capturing module and the processing module of the invention, information associated with the quality of the fresh foods can be presented objectively, detailed and in real-time, allowing the fresh foods online traders to be capable of further classifying the fresh foods to achieve more stringent quality control and product differentiation, so that the commodities become more consistent. Secondly, the industry is also capable of conveying the quality information of the fresh foods to the consumers more accurately during transactions, reducing a cognitive gap of the quality of the fresh foods between the industry and the consumers, and increasing a satisfaction level of transactions.

DETAILED DESCRIPTION OF THE PREFERRED EMBODIMENTS

The detailed description and technical content of the invention are described below with reference to the drawings.

Figure 1:
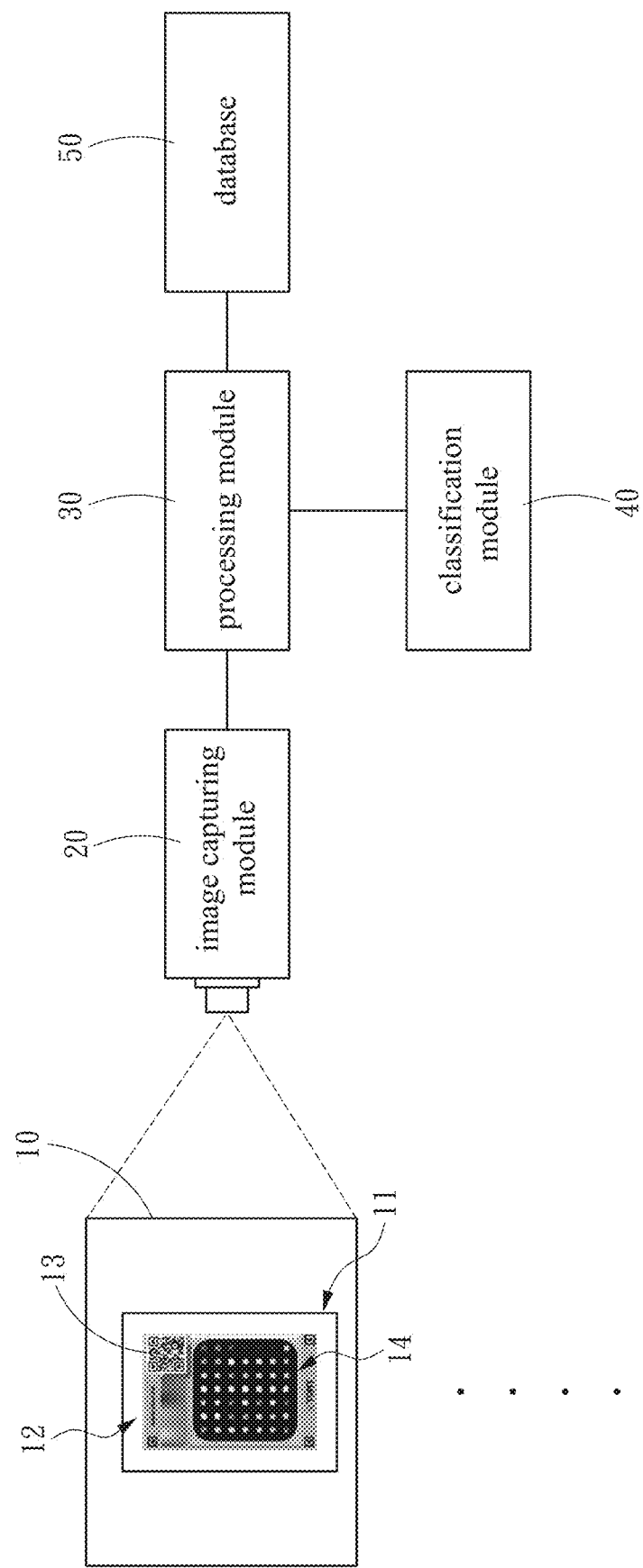
FIG. 1 is a functional block schematic diagram according to an embodiment of the invention.

Please refer to FIG. 1 for a functional block schematic diagram according to an embodiment of the invention. The invention provides a system for managing fresh foods according to a flavor thereof, comprising a plurality of fresh foods 10, an image capturing module 20, a processing module 30 and a classification module 40. A product label 11 is attached to each of the plurality of fresh foods 10, and the product label includes a thin film 12, a code 13 and a colorimetric transducer array 14. The thin film 12 is provided for the code 13 to attach thereon. The code 13 is associated with each of the plurality of fresh foods 10, and the code 13 is determined by at least one information of each of the plurality of fresh foods 10, wherein the at least one information is selected from a group consisting of a resume information, a quality information and an initial appearance. Further, the code 13 can be a string of numbers, a one-dimensional bar code, a two-dimensional bar code (QR code), and so on. The colorimetric transducer array 14 is formed on the thin film 12, and the colorimetric transducer array 14 comprises at least one sensing material for sensing each of the plurality of fresh foods 10. Each sensing material undergoes a chemical reaction with at least one metabolic molecule of each of the fresh foods 10 to change each of the at least one sensing material from an initial color to an indication color.

Figure 2B:
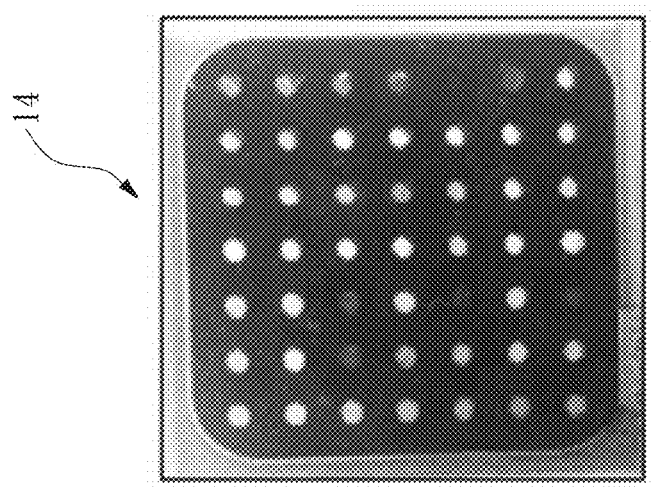
FIG. 2A and FIG. 2B are schematic diagrams of a colorimetric transducer array according to an embodiment of the invention.
Figure 2A:
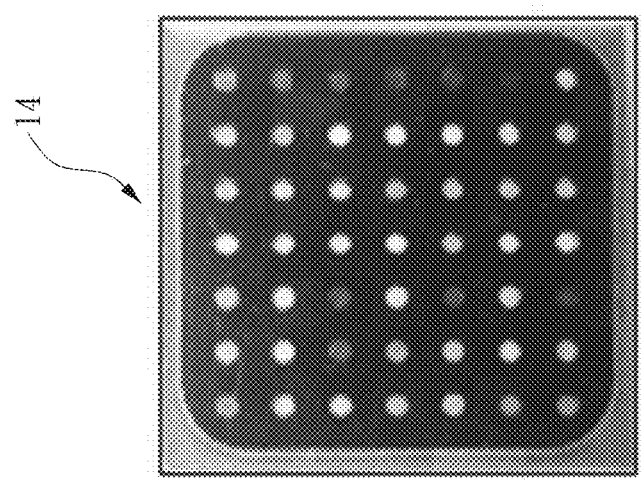

Please refer to FIG. 2A and FIG. 2B together. In one embodiment, one of the fresh foods 10 is pork, and the product label 11 can be attached to the pork. If the pork is fresh, the sensing material on the colorimetric transducer array 14 presents an indication color as shown in FIG. 2A; and if the pork is stale due to excessive storage time or being preserved improperly, the sensing material on the colorimetric transducer array 14 presents an indication color as shown in FIG. 2B.

In one embodiment, preferably there is a plurality of sensing materials which are formed on the thin film 12 in a manner similar to pixels, for example, 7×7 sensing pixels. The plurality of sensing materials is selected according to the fresh foods 10 to be applied and environment. The plurality of sensing materials comprises a color reagent, and the color reagent is selected from a group consisting of methyl red, Congo red, bromophenol blue, bromocresol purple, bromocresol green, cresol red, phenol red, thymolphthalein, resazurin, paranitrophenol, bromodaphne blue, thymol blue, neutral red, crystal violet, 4-(4-nitrobenzyl) pyridine, pyrocatechol violet, chlorophenol red, nitrozine yellow, bromophenol red, m-cresol purple, Eriochrome black T, safranine, luciferin, Eosin yellow, Brilliant green, Titan yellow, Victoria blue B, carmine, litmus, curcumin, anthocyanin, alizarin red S, alizarin yellow R, indigo carmine, nile blue A, orange yellow G, Eosin B, 3,3',5,5'-tetraiodophenol sulfone phenolphthalein, bromoxylenol blue, phenol blue, disperse orange 25, acridine orange, disperse orange 3, disperse red 1, bromopyrogallol red, diamine diphenyl sulfide maple, aminofluorescein, erythroviolet ammonium urea, 2,6-dichlorophenolindophenol, sodium salts thereof, and mixtures thereof.

In one embodiment, the at least one sensing material further comprises a molecular barrier material which is selected from a group consisting of octadecanol, polyvinylpyrrolidone, polyvinyl formal, polyvinyl acetate resin, phenolic resin, epoxy resin, polybutene resin, polyethylene glycol, carbon black, carbon nanotubes, graphene, cellulose nanofibers (CNF), and silicone compounds. The molecular barrier material is mixed with the color reagent to form the sensing pixel; or the molecular barrier material is coated on the color reagent to form the sensing pixel. The molecular barrier material is capable of affecting a reaction speed of the sensing material, and the reaction speed can be adjusted by selecting the different molecular barrier materials, to meet the requirements of use.

The image capturing module 20 captures an image. The image comprises an appearance of each of the plurality of fresh foods 10, the code 13 and the indication color. And the processing module 30 provides a real-time information according to a comparison result between the image and a database 50, wherein the real-time information is associated with a quality of each of the plurality of fresh foods 10. The real-time information can include sweetness, hardness, freshness, and so on. In addition, the classification module 40 receives the real-time information and classifies the plurality of fresh foods 10 according to the real-time information. After the plurality of fresh foods 10 are classified, the industry can adjust purchase strategy, sales method, or price according to a classification result.

A method for managing foods based on the system comprising following steps of:

step 1: providing the plurality of fresh foods 10, attaching the product label 11 on each of the plurality of fresh foods 10, the product label 11 including the thin film 12, the code 13 and the colorimetric transducer array 14, the colorimetric transducer array 14 comprising the at least one sensing material for sensing the plurality of fresh foods 10, the at least one sensing material undergoing the chemical reaction with the at least one metabolic molecule of each of the fresh foods 10 to change the at least one sensing material from the initial color to the indication color;

step 2: capturing the image, the image comprising the appearance of each of the plurality of fresh foods 10, the code 13 and the indication color;

step 3: providing the real-time information of each of the plurality of fresh foods 10 according to the comparison result between the image and the database 50;

step 4: generating the classification result for the quality of each of the plurality of fresh foods 10 according to the real-time information; and step 5: classifying each of the plurality of fresh foods 10 according to the classification result.

The invention further provides a method for trading foods, comprising following steps of:

step 1: providing the plurality of fresh foods 10, attaching the product label 11 on each of the plurality of fresh foods 10, the product label 11 including the thin film 12, the code 13 and the colorimetric transducer array 14, the colorimetric transducer array 14 comprising the at least one sensing material for sensing each of the plurality of fresh foods 10, the at least one sensing material undergoing the chemical reaction with the at least one metabolic molecule of each of the plurality of fresh foods 10 to change the at least one sensing material from the initial color to the indication color;

step 2: capturing the image, the image comprising the appearance of each of the plurality of fresh foods 10, the code 13 and the indication color;

step 3: providing the real-time information of each of the plurality of fresh foods 10 according to the comparison result between the image and the database 50;

step 4: generating the classification result for the quality of each of the plurality of fresh foods 10 according to the real-time information; and step 5: classifying each of the plurality of fresh foods 10 according to the classification result; and step 6: using the classification result as a part of a sales information of each of the plurality of fresh foods 10 and displaying the classification result to at least one consumer for selecting and purchasing each of the plurality of fresh foods 10 according to the classification result.

In detail, the invention provides consumers with the classification result as the sales information, so that the consumers are able to know the real-time information of the plurality of fresh foods 10 and can accurately learn about the quality of the plurality of fresh foods 10, such as sweetness, hardness, freshness, etc., as a reference for purchase.

Figure 3:
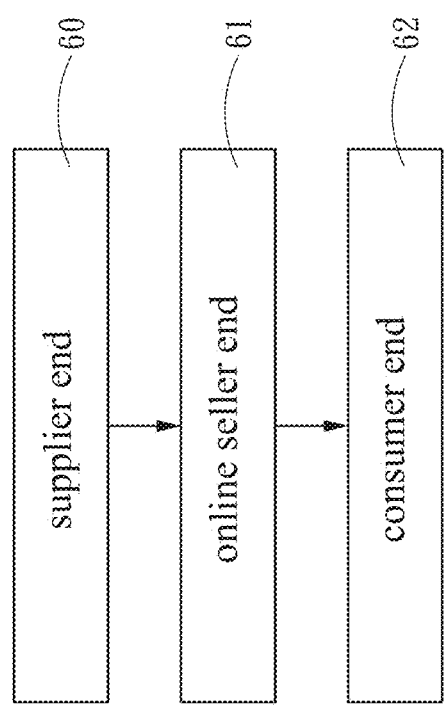
FIG. 3 is a functional block schematic diagram according to another embodiment of the invention.

Please refer to FIG. 3 for a functional block diagram of another embodiment of the invention. Through the system of the invention, the invention can be applied to both business to business (B2B) and business to consumer (B2C) online business models, and can be used for transactions and management among a supplier end 60, an online seller end 61 and a consumer end 62.

For the supplier end 60, a supplier directly attaches the product label 11 on the fresh foods 10 to be supplied, and uses the image capturing module 20 to capture the image of the colorimetric transducer array 14 and obtain the indication color and learn about the real-time information. In addition, the database 50 for generating the real-time information by comparing with the indication color is also established by the supplier according to past data.

For the online seller end 61, an online seller can instruct the supplier, a delivery end, and a warehouse to use the image capturing module 20 to capture the image of the colorimetric transducer array 14 at each stage or timing, and obtain the indication color and generate the real-time information by comparing with the database 50, so that the online seller can confirm whether the real-time information (quality) of the fresh foods 10 has been changed, and the online seller can use the real-time information as a basis for classification to generate the classification result, and the classification result (i.e., the real-time information) is used as a part of the sales information and displayed to the consumers, for determining pricing accordingly. In addition, the real-time information is also used by the online seller to properly handle the fresh foods 10. For example, if the quality of the real-time information shows that the quality is poor, the supplier can be required to reduce the price; and if the quality does not have any sales value, a whole batch of the fresh foods 10 can be returned. Further, the real-time information can be combined with blockchain technology to ensure the correctness of the product resume provided by the supplier, and to effectively ensure that the quality of the fresh foods 10 provided by the supplier meets the demands of the online seller. In a sales stage, the online seller also uses the real-time information of the fresh foods 10 to know the quality of the fresh foods 10 at any time and remind the consumers. For example, at the beginning of a sale, if the fresh foods 10 are fruits that best before dates have not passed, the consumers can be reminded to eat later; the consumers can use a camera at hand to take pictures for capturing the image of the colorimetric transducer array 14 at any time, and send the pictures to the online seller to confirm whether the best before dates have passed. When the best before dates are about to pass, the online seller can lower the price to speed up sales and remind the consumers to eat as soon as possible. In storage or transportation stage, when the fresh foods 10 has been losing freshness that the fresh foods 10 cannot be sold, and the fresh foods 10 can be destroyed.

At the consumer end 62, the consumers purchase the fresh foods 10 based on the sales information, and make appropriate disposals through the real-time information at any time. If the quality of the fresh foods 10 shown in the real-time information does not meet the demands, the consumers can refuse to accept the fresh foods 10, or request a refund.

Accordingly, by coordinating the colorimetric transducer array with the image capturing module and the processing module of the invention, the at least one information associated with the quality of the fresh foods can be presented objectively, detailedly and in real-time, allowing the fresh foods online traders to be capable of further classifying the fresh foods to achieve more stringent quality control and product differentiation, so that commodities become more consistent; secondly, an industry is also capable of conveying the quality information of the fresh foods to the consumers more accurately during transactions, reducing a cognitive gap of the quality of the fresh foods between the industry and the consumers, and increasing a satisfaction level of transactions.

What is claimed is:

1. A system for managing foods according to a flavor thereof, comprising:

a plurality of fresh foods, each of the plurality of fresh foods attached with a product label, the product label including a thin film, a code provided on the thin film and associated with each of the plurality of fresh foods, and a colorimetric transducer array formed on the thin film, the colorimetric transducer array comprising at least one sensing material for sensing the plurality of fresh foods, each of the at least one sensing material undergoing a chemical reaction with at least one metabolic molecule of each of the fresh foods to change each of the at least one sensing material from an initial color to an indication color;

an image capturing module, capturing an image, the image comprising an appearance of each of the plurality of fresh foods, the code and the indication color;

a processing module, providing a real-time information associated with a quality of each of the plurality of fresh foods according to a comparison result between the image and a database; and a classification module, receiving the real-time information and classifying the plurality of fresh foods according to the real-time information.

2. The system as claimed in claim 1, wherein the sensing material comprises a color reagent, and the color reagent is selected from a group consisting of methyl red, Congo red, bromophenol blue, bromocresol purple, bromocresol green, cresol red, phenol red, thymolphthalein, resazurin, paranitrophenol, bromodaphne blue, thymol blue, neutral red, crystal violet, 4-(4-nitrobenzyl) pyridine, pyrocatechol violet, chlorophenol red, nitrozine yellow, bromophenol red, m-cresol purple, Eriochrome black T, safranine, luciferin, Eosin yellow, Brilliant green, Titan yellow, Victoria blue B, carmine, litmus, curcumin, anthocyanin, alizarin red S, alizarin yellow R, indigo carmine, nile blue A, orange yellow G, Eosin B, 3,3',5,5'-tetraiodophenol sulfone phenolphthalein, bromoxylenol blue, phenol blue, disperse orange 25, acridine orange, disperse orange 3, disperse red 1, bromopyrogallol red, diamine diphenyl sulfide maple, aminofluorescein, erythroviolet ammonium urea, 2,6-dichloroindophenol, sodium salts thereof, and mixtures thereof.

3. The system as claimed in claim 1, wherein the sensing material comprises a molecular barrier material, and the molecular barrier material is selected from a group consisting of octadecanol, polyvinylpyrrolidone, polyvinyl formal, polyvinyl acetate resin, phenolic resin, epoxy resin, polybutene resin, polyethylene glycol, carbon black, carbon nanotubes, graphene, cellulose nanofibers, and silicone compounds.

4. A method for managing foods according to a flavor thereof, comprising following steps of:
providing a plurality of fresh foods, attaching a product label on each of the plurality of fresh foods, the product label comprising a thin film, a code provided on the thin film and associated with each of the plurality of fresh foods, and a colorimetric transducer array formed on the thin film, the colorimetric transducer array comprising at least one sensing material for sensing the plurality of fresh foods, each of the at least one sensing material undergoing a chemical reaction with at least one metabolic molecule of each of the plurality of fresh foods to change each of the at least one sensing material from an initial color to an indication color;
capturing an image, the image comprising an appearance of each of the plurality of fresh foods, the code and the indication color;
providing a real-time information associated with a quality of each of the plurality of fresh foods according to a comparison result between the image and a database;
generating a classification result for the quality of each of the plurality of fresh foods according to the real-time information; and
classifying each of the plurality of fresh foods according to the classification result.

5. The method as claimed in claim 4, wherein the sensing material comprises a color reagent, and the color reagent is selected from a group consisting of methyl red, Congo red, bromophenol blue, bromocresol purple, bromocresol green, cresol red, phenol red, thymolphthalein, resazurin, paranitrophenol, bromodaphne blue, thymol blue, neutral red, crystal violet, 4-(4-nitrobenzyl) pyridine, pyrocatechol violet, chlorophenol red, nitrozine yellow, bromophenol red, m-cresol purple, Eriochrome black T, safranine, luciferin, Eosin yellow, Brilliant green, Titan yellow, Victoria blue B, carmine, litmus, curcumin, anthocyanin, alizarin red S, alizarin yellow R, indigo carmine, nile blue A, orange yellow G, Eosin B, 3,3',5,5'-tetraiodophenol sulfone phenolphthalein, bromoxylenol blue, phenol blue, disperse orange 25, acridine orange, disperse orange 3, disperse red 1, bromopyrogallol red, diamine diphenyl sulfide maple, aminofluorescein, erythroviolet ammonium urea, 2,6-dichloroindophenol, sodium salts thereof, and mixtures thereof.

6. The method as claimed in claim 4, wherein the sensing material comprises a molecular barrier material, and the molecular barrier material is selected from a group consisting of octadecanol, polyvinylpyrrolidone, polyvinyl formal, polyvinyl acetate resin, phenolic resin, epoxy resin, polybutene resin, polyethylene glycol, carbon black, carbon nanotubes, graphene, cellulose nanofibers, and silicone compounds.

7. A method for trading foods, comprising following steps of:
providing a plurality of fresh foods, attaching a product label on each of the plurality of fresh foods, the product label comprising a thin film, a code provided on the thin film and associated with each of the plurality of fresh foods, and a colorimetric transducer array formed on the thin film, the colorimetric transducer array comprising at least one sensing material for sensing each of the plurality of fresh foods, each of the at least one sensing material undergoing a chemical reaction with at least one metabolic molecule of each of the plurality of fresh foods to change each of the at least one sensing material from an initial color to an indication color;
capturing an image, the image comprising an appearance of each of the plurality of fresh foods, the code and the indication color;
providing a real-time information associated with a quality of each of the plurality of fresh foods according to a comparison result between the image and a database;
generating a classification result for the quality of each of the plurality of fresh foods according to the real-time information; and
using the classification result as a part of a sales information of each of the plurality of fresh foods and displaying the classification result to at least one consumer for selecting and purchasing each of the plurality of fresh foods according to the classification result.

8. The method as claimed in claim 7, wherein the sensing material comprises a color reagent, and the color reagent is selected from a group consisting of methyl red, Congo red, bromophenol blue, bromocresol purple, bromocresol green, cresol red, phenol red, thymolphthalein, resazurin, paranitrophenol, bromodaphne blue, thymol blue, neutral red, crystal violet, 4-(4-nitrobenzyl) pyridine, pyrocatechol violet, chlorophenol red, nitrozine yellow, bromophenol red, m-cresol purple, Eriochrome black T, safranine, luciferin, Eosin yellow, Brilliant green, Titan yellow, Victoria blue B, carmine, litmus, curcumin, anthocyanin, alizarin red S, alizarin yellow R, indigo carmine, nile blue A, orange yellow G, Eosin B, 3,3',5,5'-tetraiodophenol sulfone phenolphthalein, bromoxylenol blue, phenol blue, disperse orange 25, acridine orange, disperse orange 3, disperse red 1, bromopyrogallol red, diamine diphenyl sulfide maple, aminofluorescein, erythroviolet ammonium urea, 2,6-dichloroindophenol, sodium salts thereof, and mixtures thereof.

9. The method as claimed in claim 7, wherein the sensing material comprises a molecular barrier material, and the molecular barrier material is selected from a group consisting of octadecanol, polyvinylpyrrolidone, polyvinyl formal, polyvinyl acetate resin, phenolic resin, epoxy resin, polybutene resin, polyethylene glycol, carbon black, carbon nanotubes, graphene, cellulose nanofibers, and silicone compounds.

\* \* \* \* \*